United States Patent
Goble et al.

(10) Patent No.: US 7,399,302 B2
(45) Date of Patent: *Jul. 15, 2008

(54) APPARATUS AND METHOD FOR RECONSTRUCTING A LIGAMENT

(75) Inventors: Eugene Marlowe Goble, Alta, WY (US); Daniel F. Justin, Logan, UT (US)

(73) Assignee: DePuy Mitek, Inc., Raynham, MA (US)

( * ) Notice: Subject to any disclaimer, the term of this patent is extended or adjusted under 35 U.S.C. 154(b) by 196 days.

This patent is subject to a terminal disclaimer.

(21) Appl. No.: 10/648,688

(22) Filed: Aug. 25, 2003

(65) Prior Publication Data

US 2004/0097977 A1    May 20, 2004

Related U.S. Application Data

(63) Continuation of application No. 09/634,162, filed on Aug. 9, 2000, now Pat. No. 6,610,064.

(60) Provisional application No. 60/148,005, filed on Aug. 10, 1999.

(51) Int. Cl.
*A61B 17/56* (2006.01)

(52) U.S. Cl. ........................... 606/72; 606/99

(58) Field of Classification Search ............ 606/99, 606/74, 72

See application file for complete search history.

(56) References Cited

U.S. PATENT DOCUMENTS

| | | | |
|---|---|---|---|
| 5,092,868 A * | 3/1992 | Mehdian | 606/74 |
| 5,139,520 A | 8/1992 | Rosenberg | |
| 5,234,435 A | 8/1993 | Seagrave, Jr. | |
| 5,266,075 A * | 11/1993 | Clark et al. | 606/138 |
| 5,350,380 A | 9/1994 | Goble et al. | |
| 5,356,413 A | 10/1994 | Martins et al. | |
| 5,393,302 A * | 2/1995 | Clark et al. | 606/72 |
| 5,397,356 A | 3/1995 | Goble et al. | |
| 5,431,651 A | 7/1995 | Goble | |
| 5,601,562 A | 2/1997 | Wolf et al. | |
| 5,603,716 A * | 2/1997 | Morgan et al. | 606/88 |
| 5,674,224 A | 10/1997 | Howell et al. | |
| 5,891,150 A | 4/1999 | Chan | |

(Continued)

FOREIGN PATENT DOCUMENTS

| | | |
|---|---|---|
| EP | 0931514 A2 | 7/1999 |
| WO | WO 99/15095 A1 | 4/1999 |

*Primary Examiner*—Michael J. Hayes
*Assistant Examiner*—Michael G. Mendoza
(74) *Attorney, Agent, or Firm*—Nutter McClennen & Fish LLP

(57) ABSTRACT

A system for securing a graft ligament in a bone tunnel, a flexible member for positioning the graft ligament in the bone tunnel, the flexible member having a first closed loop at a first end thereof and a second closed loop at a second end thereof, a delivery device having an end for positioning the first and second loops of the flexible member in the bone tunnel, and a pulling member having an end for withdrawing a selected one of the ends of the flexible member from the delivery device when the delivery device is positioned in the bone tunnel, and for pulling the selected end of the flexible member through a portion of a second bone tunnel which intersects, and extends traverse to, the first-mentioned bone tunnel.

11 Claims, 12 Drawing Sheets

U.S. PATENT DOCUMENTS

| | | |
|---|---|---|
| 5,918,604 A | 7/1999 | Whelan |
| 6,113,604 A | 9/2000 | Whittaker et al. |
| 6,152,928 A | 11/2000 | Wenstrom, Jr. |
| 6,267,767 B1 | 7/2001 | Strobel et al. |
| 6,499,486 B1 | 12/2002 | Chervitz et al. |
| 6,808,528 B2 | 10/2004 | Justin |

* cited by examiner

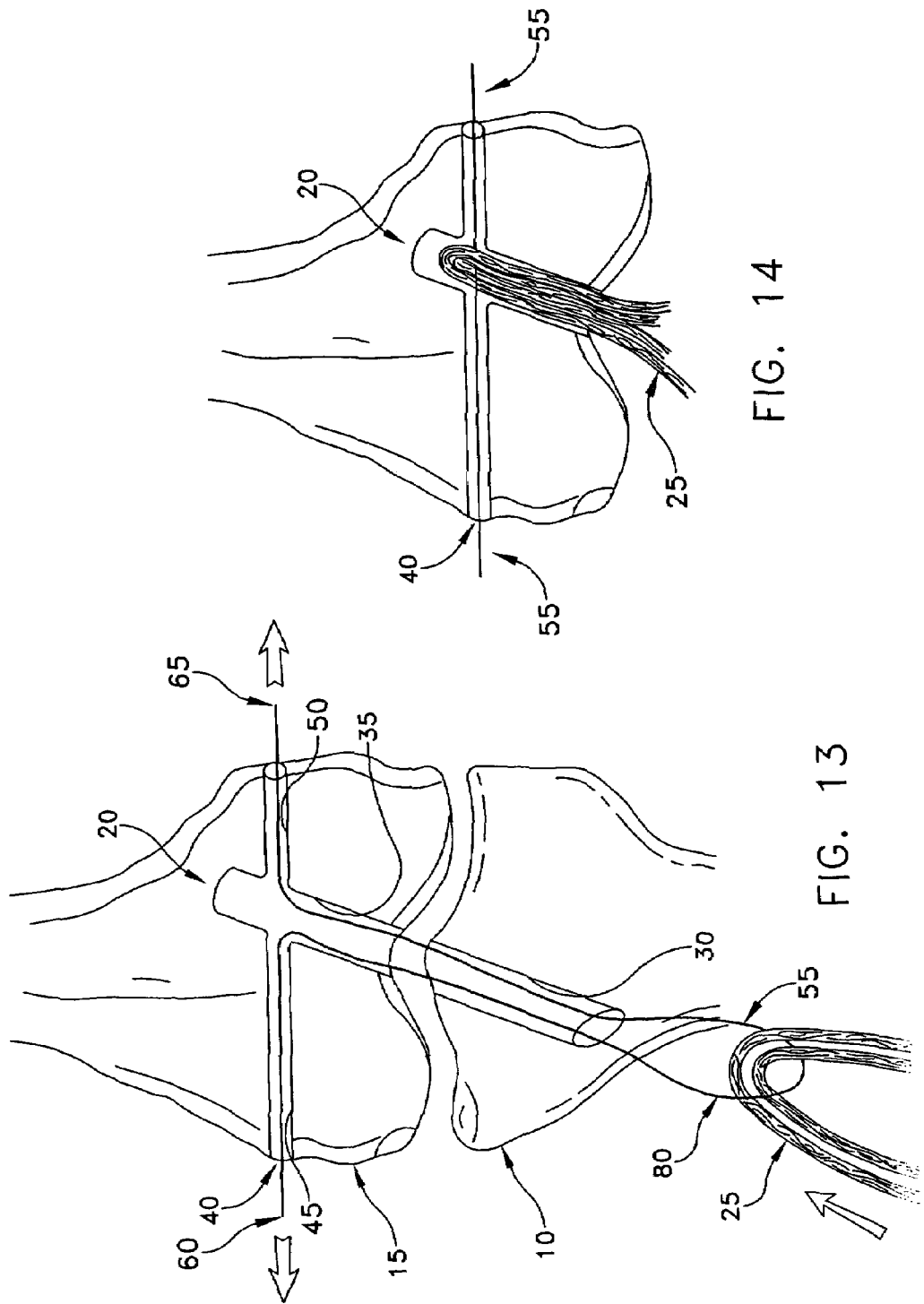

APPARATUS AND METHOD FOR RECONSTRUCTING A LIGAMENT

REFERENCE TO PENDING PRIOR PATENT APPLICATION

This patent application is a continuation of prior U.S. patent application Ser. No. 09/634,162 filed Aug. 9, 2000 now U.S. Pat. No. 6,610,064 by Eugene Marlowe Goble et al. for APPARATUS AND METHOD FOR RECONSTRUCTING A LIGAMENT, which in turn claims benefit of now abandoned prior U.S. Provisional Patent Application Ser. No. 60/148,005, filed Aug. 10, 1999 by Eugene Marlowe Goble for METHOD OF DELIVERING AN ACL GRAFT, which patent application is hereby incorporated herein by reference.

FIELD OF THE INVENTION

This invention relates to medical devices and procedures in general, and more particularly to medical devices and procedures for reconstructing a ligament.

BACKGROUND OF THE INVENTION

A ligament is a piece of fibrous tissue which connects one bone to another.

Ligaments are frequently damaged (e.g., detached or torn or ruptured, etc.) as the result of injury and/or accident. A damaged ligament can impede proper motion of a joint and cause significant pain.

Various procedures have been developed to repair or replace a damaged ligament. The specific procedures used depend on the particular ligament which is to be restored and on the extent of the damage.

One ligament which is frequently damaged as the result of injury and/or accident is the anterior cruciate ligament (ACL). Looking now at FIG. 1, the ACL 5 extends between the top of the tibia 10 and the bottom of the femur 15. A damaged ACL can cause instability of the knee joint and cause substantial pain and arthritis.

Numerous procedures have been developed to restore the ACL through a graft ligament replacement. In general, and looking now at FIG. 2, these ACL replacement procedures involve drilling a bone tunnel 20 through tibia 10 and up into femur 15. Then a graft ligament 25, consisting of a harvested or artificial ligament or tendon(s), is passed through the tibial portion 30 of tunnel 20 (sometimes referred to as "the tibial tunnel"), across the interior of the joint, and up into the femoral portion 35 of tunnel 20 (sometimes referred to as "the femoral tunnel"). Then a distal portion of graft ligament 25 is secured in femoral tunnel 35, and a proximal portion of graft ligament 25 is secured in tibial tunnel 30.

There are numerous ways in which graft ligament 25 may be positioned in tunnel 20 and secured in position.

One such way is disclosed in U.S. Pat. No. 5,918,604, issued Jul. 6, 1999 to Whelan for METHOD OF LOADING TENDONS INTO THE KNEE. According to this patent, the ligament may be towed up tibial tunnel 30 and femoral tunnel 35 and then secured in femoral tunnel 35 with a crosspin.

More particularly, and looking now at FIG. 3, the bone tunnel 20 is formed by drilling through tibia 10 and up into femur 15, whereby to form tibial tunnel 30 and femoral tunnel 35. Then a transverse bone tunnel 40 is formed in femur 15 so that transverse bone tunnel 40 intersects femoral tunnel 35. Bone tunnel 20 bifurcates transverse bone tunnel 40 into two tunnel portions, a first transverse bone tunnel portion 45 and a second transverse bone tunnel portion 50.

After transverse bone tunnel 40 has been formed, a flexible member 55 is used to draw graft ligament 25 up into place.

More particularly, according to the aforementioned U.S. Pat. No. 5,918,604, this is done by threading flexible member 55 through transverse bone tunnel 40. Then a crochet-hook device (not shown in FIG. 3) is passed up tibial tunnel 30, across the interior of the knee joint, and up femoral tunnel 35. The crochet-hook device is used to hook flexible member 55 at the intersection of transverse bone tunnel 40 and femoral tunnel 35. Then the crochet-hook device is used to pull flexible member 55 down femoral tunnel 35, across the interior of the knee joint, down tibial tunnel 30, and out the front side of tibia 10. Next, graft ligament 25 is looped over flexible member 55 (FIG. 3). One or both free ends of flexible member 55 is/are then pulled away from femur 15, whereby to pull flexible member 55, and hence the looped graft ligament 25, up tibial tunnel 30, across the interior of the knee joint, and then up into femoral tunnel 35. (FIG. 4).

Once flexible member 55 and graft ligament 25 have assumed the position shown in FIG. 4, the graft ligament may be retained in that position by passing a cannulated crosspin 57 over flexible member 55 and into transverse bone tunnel 40 so that the crosspin 57 extends under graft ligament 25 and supports the looped graft ligament 25 within femoral tunnel 35. Then flexible member 55 is withdrawn from the surgical site.

Unfortunately, the method taught in U.S. Pat. No. 5,918,604 suffers from a number of drawbacks.

For one thing, use of this method can result in erosion of the patient's bone. More particularly, and looking now at F*ig*. 5, flexible member 55 must first be drawn down femoral tunnel 35, across the interior of the knee joint, and then down tibial tunnel 30 in order to pick up graft ligament 25; and then later, flexible member 55 must be drawn back up tibial tunnel 30, across the interior of the knee joint, and then back up femoral tunnel 35 in order to carry graft ligament 25 into position. These actions cause flexible member 55 to engage the bone which is located at the intersection of femoral tunnel 35 and transverse bone tunnel 40, i.e., to engage the bone edges 59 (FIG. 5) as the flexible member 55 is drawn down the femoral tunnel 35 and the tibial tunnel 30 and, again, as the flexible member 55 is drawn back up the tibial tunnel 30 and the femoral tunnel 35. This engagement between flexible member 55 and bone edges 59 can cause bone edges 59 to be eroded. This erosion can be particularly significant where substantial forces are required to draw flexible member 55 out of bone tunnel 20 (e.g., where flexible member 55 is a metallic flexible member with significant resiliency).

For another thing, the method taught in U.S. Pat. No. 5,918,604 can be tedious to practice. More particularly, when flexible member 55 is threaded through transverse bone tunnel 40, the crochet-hook device (not shown) must be passed up tibial tunnel 30, across the interior of the knee joint, and up femoral tunnel 35. The crochet-hook device must then be manipulated to hook flexible member 55 at the intersection of femoral tunnel 35 and transverse bone tunnel 40. This is typically done without the assistance of visualization and may require several attempts before flexible member 55 is successfully hooked.

Furthermore, using the procedure taught in U.S. Pat. No. 5,918,604 may cause the flexible member 55 to twist, thus creating additional damaging forces in femoral bone tunnel 35, tibial bone tunnel 30 and/or transverse bone tunnel 40, and/or to the graft ligament 25.

OBJECTS OF THE INVENTION

As a result, an object of the present invention is to provide an improved method for reconstructing a ligament.

And another object of the present invention is to provide an improved method for reconstructing a ligament which substantially avoids various problems associated with the prior art.

SUMMARY OF THE INVENTION

These and other objects of the present invention are addressed by a novel method and apparatus for reconstructing a ligament.

In one preferred form of the invention, the invention comprises a method for securing a graft ligament in a bone tunnel, the method comprising the steps of: (1) forming a first bone tunnel in a bone, and forming a second bone tunnel in the same bone, the second bone tunnel being transverse to, and intersecting, the first bone tunnel, the second bone tunnel having first and second portions extending from the first bone tunnel; (2) positioning the first and second ends of a flexible member within the first bone tunnel such that the first and second ends are located adjacent to the intersection of the second bone tunnel with the first bone tunnel, and extracting the first and second ends out of the first and second portions of the second bone tunnel, respectively, and positioning the graft ligament over a portion of the flexible member extending out of the first bone tunnel; and (3) pulling the ends of the flexible member so as to draw the graft ligament into the first bone tunnel.

In a preferred form of the invention, the invention also comprises apparatus for securing a graft ligament in a bone tunnel, the apparatus comprising a flexible member delivery device having a suture holder for carrying the ends of a flexible member into the bone tunnel and being cannulated for receiving an arthroscope within said cannulated delivery device.

Additionally, in a preferred form of the invention, the invention comprises a system for securing a graft ligament in a bone tunnel, the system comprising a flexible member for positioning the graft ligament in the bone tunnel, a flexible member delivery device having an end for positioning the two ends of the flexible member in the bone tunnel, and a pulling member having an end for withdrawing one end of the flexible member from the delivery device positioned in the bone tunnel and pulling that end of the flexible member through a portion of a second bone tunnel which intersects, and extends transverse to, the first-mentioned bone tunnel.

BRIEF DESCRIPTION OF THE DRAWINGS

The above and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 6 and 10-15 are schematic front views of a knee joint, illustrating a novel procedure for positioning a graft ligament in a bone tunnel and securing it in position.

DETAILED DESCRIPTION OF THE INVENTION

The present invention comprises a novel method and apparatus for reconstructing a ligament.

Figure 1:
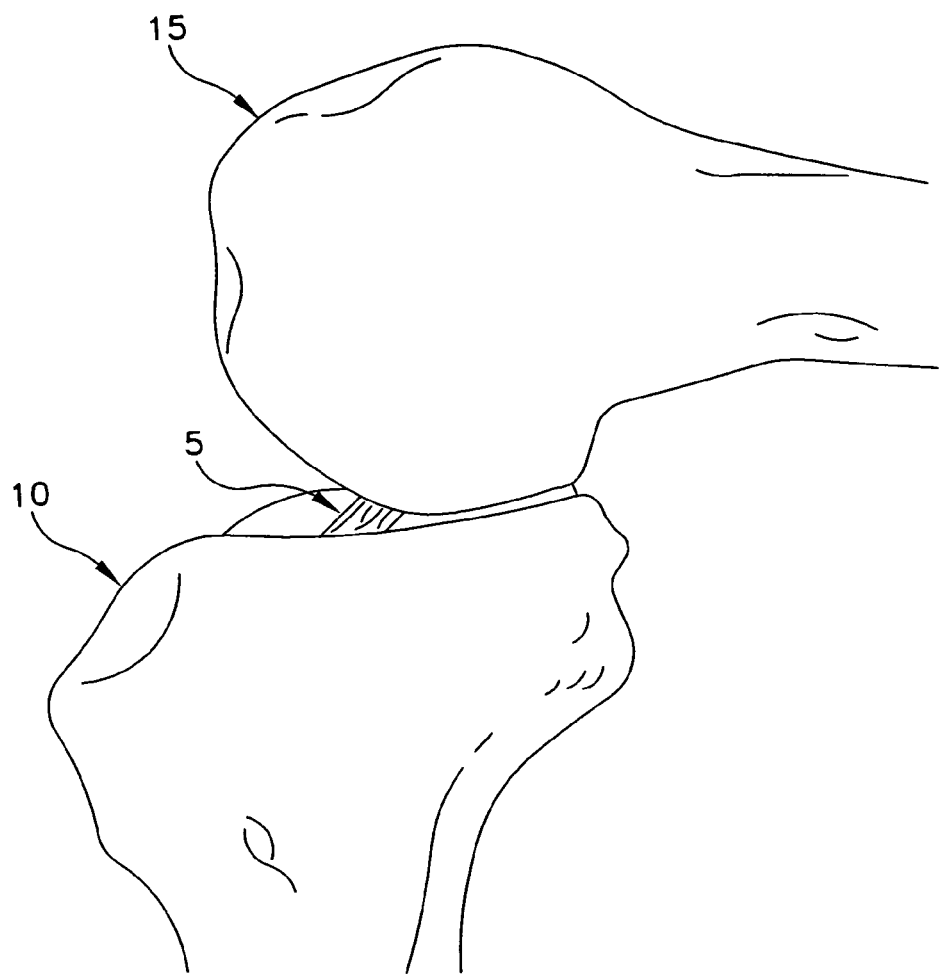
FIG. 1 is a schematic side view of a knee joint, showing an ACL extending between the top of the tibia and the bottom of the femur.
Figure 2:
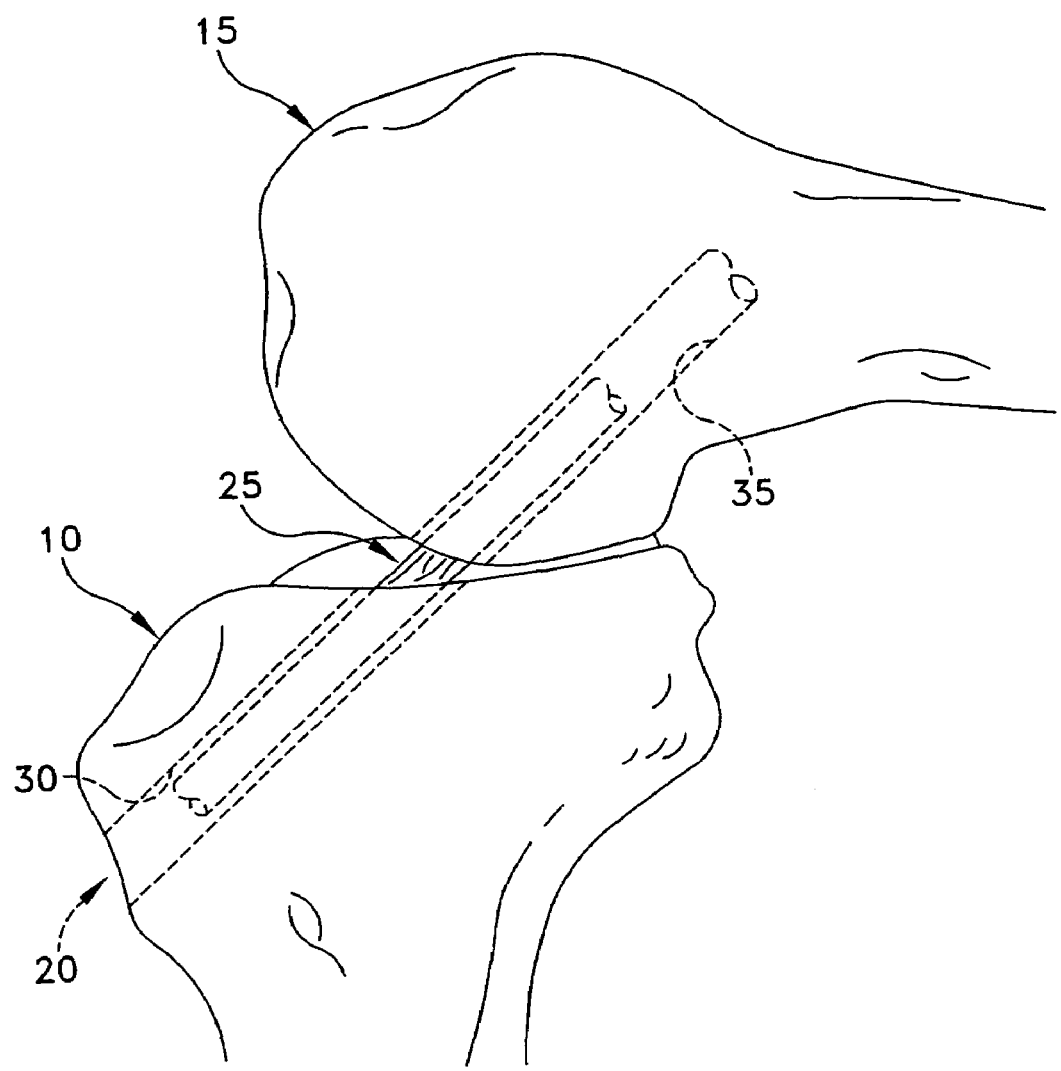
FIG. 2 is a schematic side view of the same knee joint, except showing portions of an ACL reconstruction.
Figure 3:
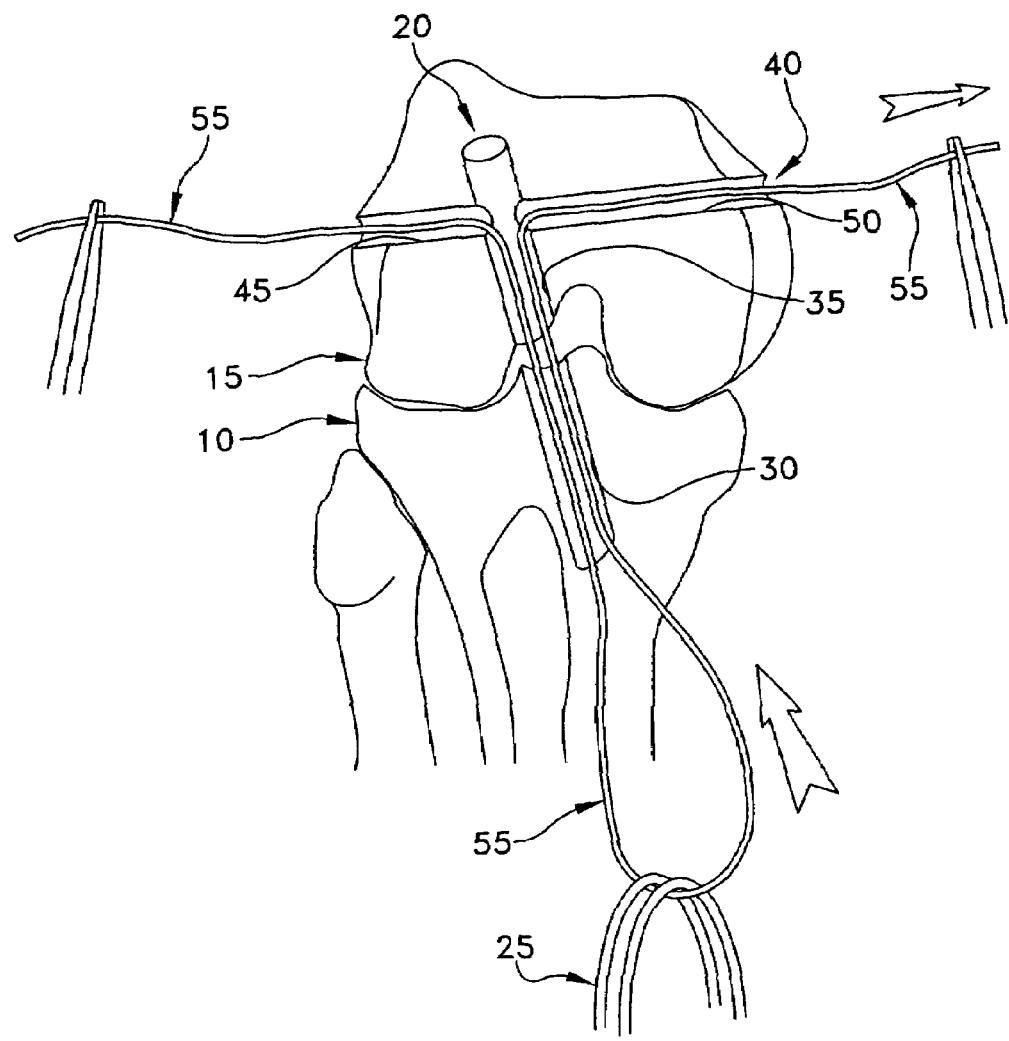
FIGS. 3-5 are schematic front views of a knee joint, illustrating various aspects of a prior art procedure for positioning a graft ligament in a bone tunnel and securing it in position.
Figure 4:
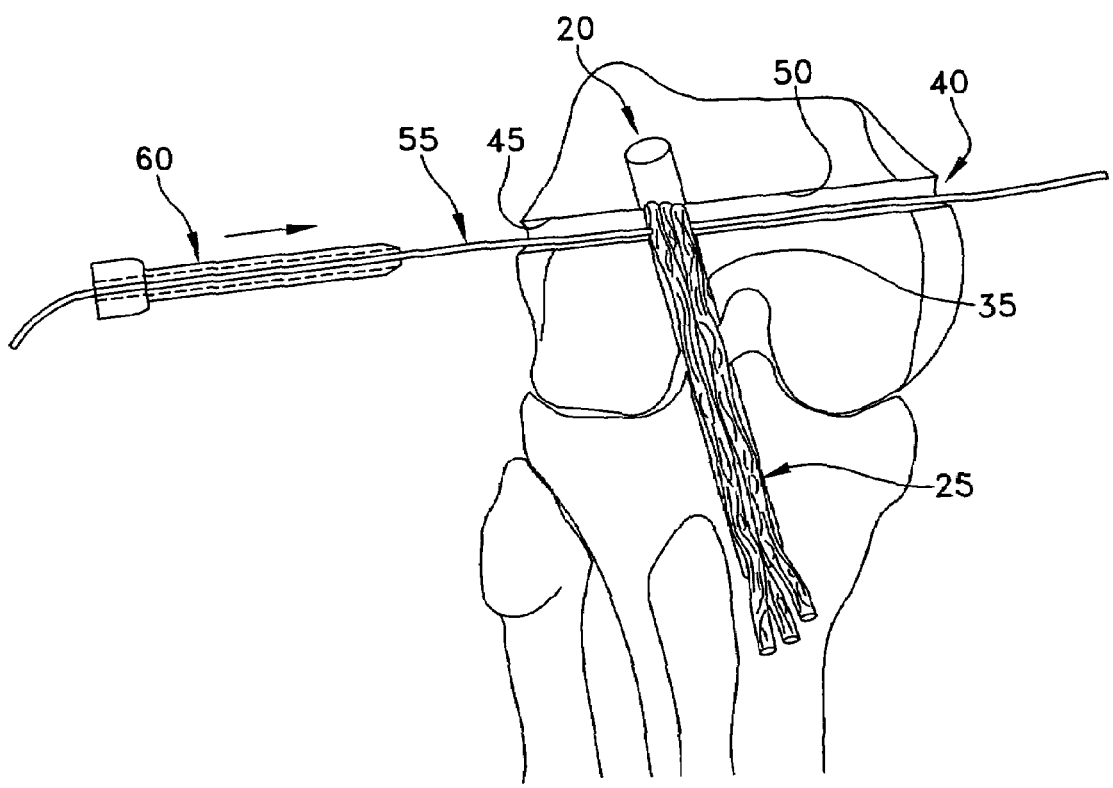
Figure 5:
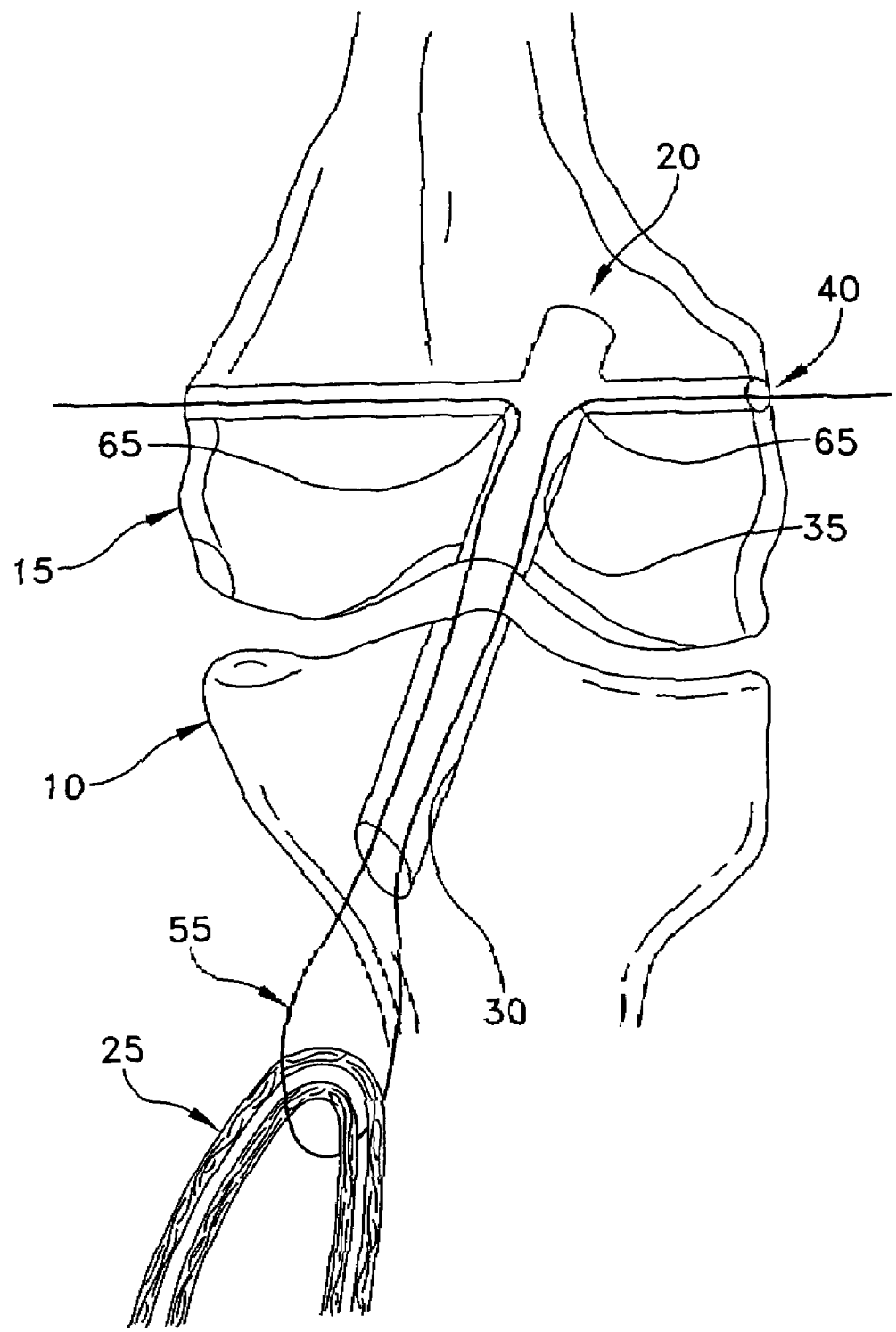
Figure 6:
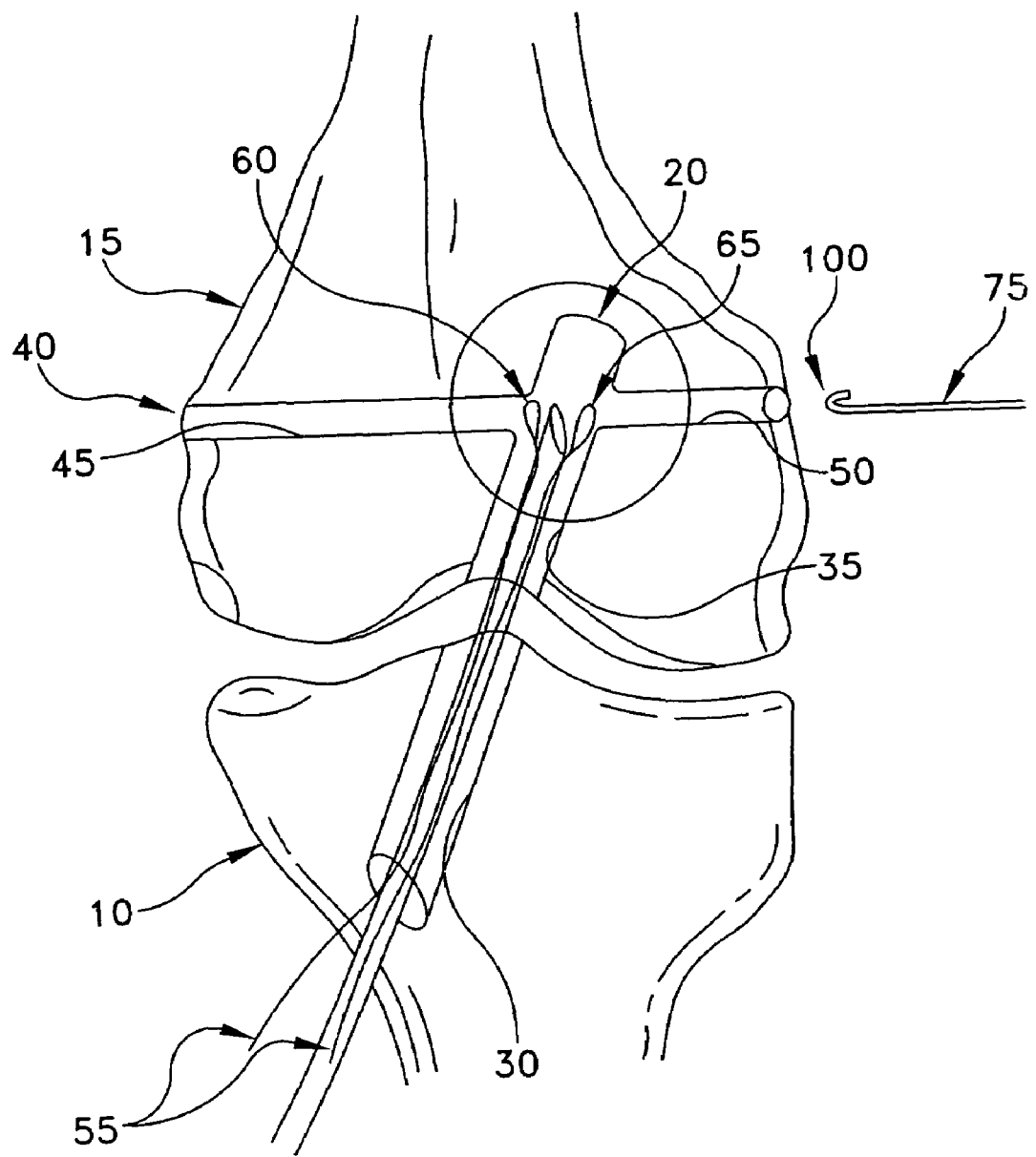

More particularly, and looking now at FIG. 6, the bone tunnel 20 is formed by drilling through tibia 10 and up into femur 15, whereby to form tibial tunnel 30 and femoral tunnel 35. Then the transverse bone tunnel 40 is formed in femur 15 so that transverse bone tunnel 40 intersects femoral tunnel 35. Bone tunnel 20 bifurcates transverse bone tunnel 40 into two tunnel portions, a first transverse bone tunnel portion 45 and a second bone tunnel portion 50.

After transverse bone tunnel 40 has been formed, a flexible member 55 is passed up bone tunnel 20. Flexible member 55 has first and second ends 60, 65. First and second ends 60, 65 are passed up tibial tunnel 30, across the interior of the knee joint, and up femoral tunnel 35. This may be done by placing first and second ends 60, 65 on the distal end of a delivery device 70, e.g., in the manner shown in FIGS. 6-9, and then inserting delivery device 70 (and hence first and second ends 60, 65 of flexible member 55) up tibial tunnel 30, across the interior of the knee joint, and then up femoral tunnel 35. Ends 60, 65 are held to the delivery device 70 in ways which will be discussed in more detail below.

Figure 10:
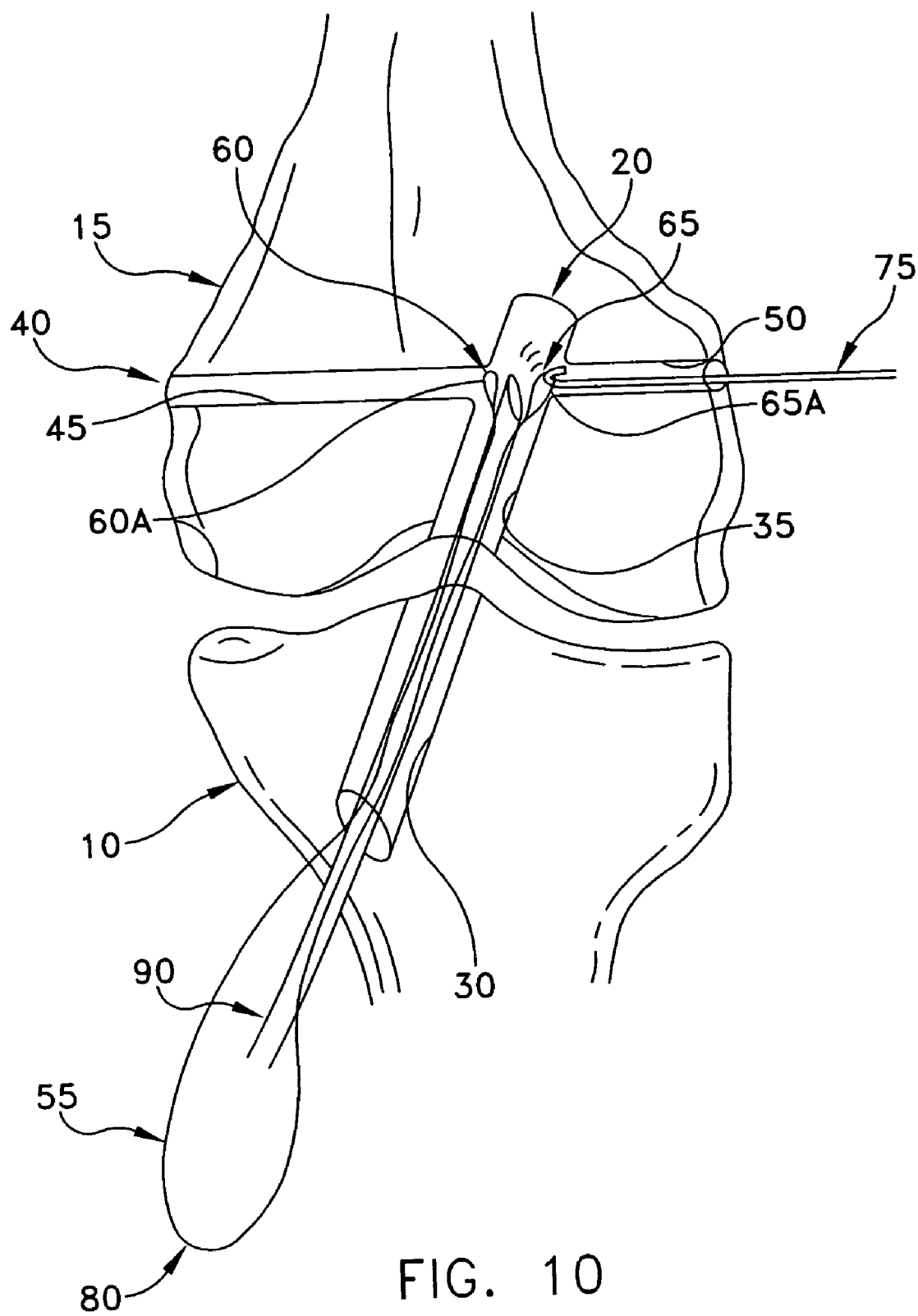
Figure 11:
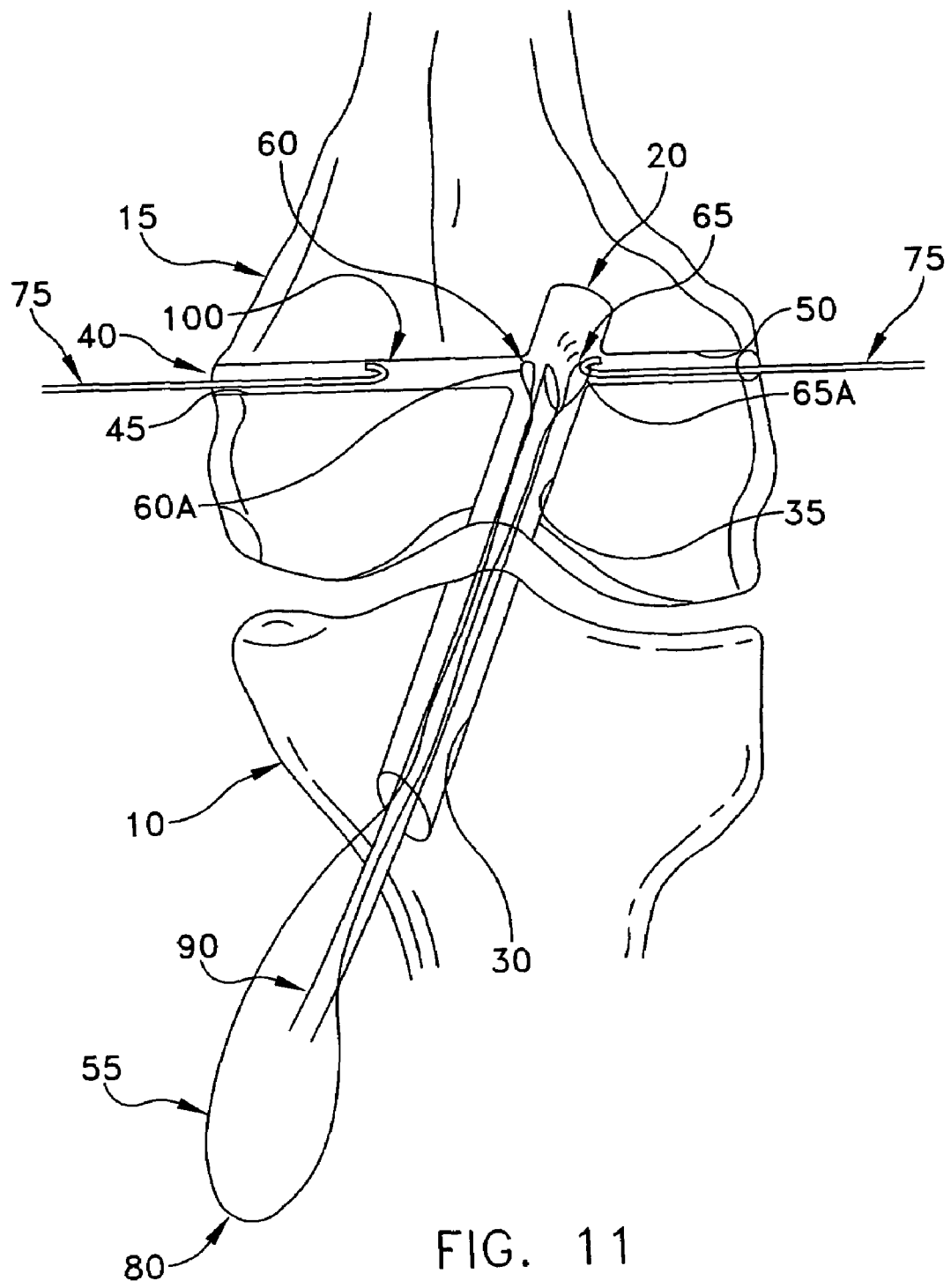
Figure 12:
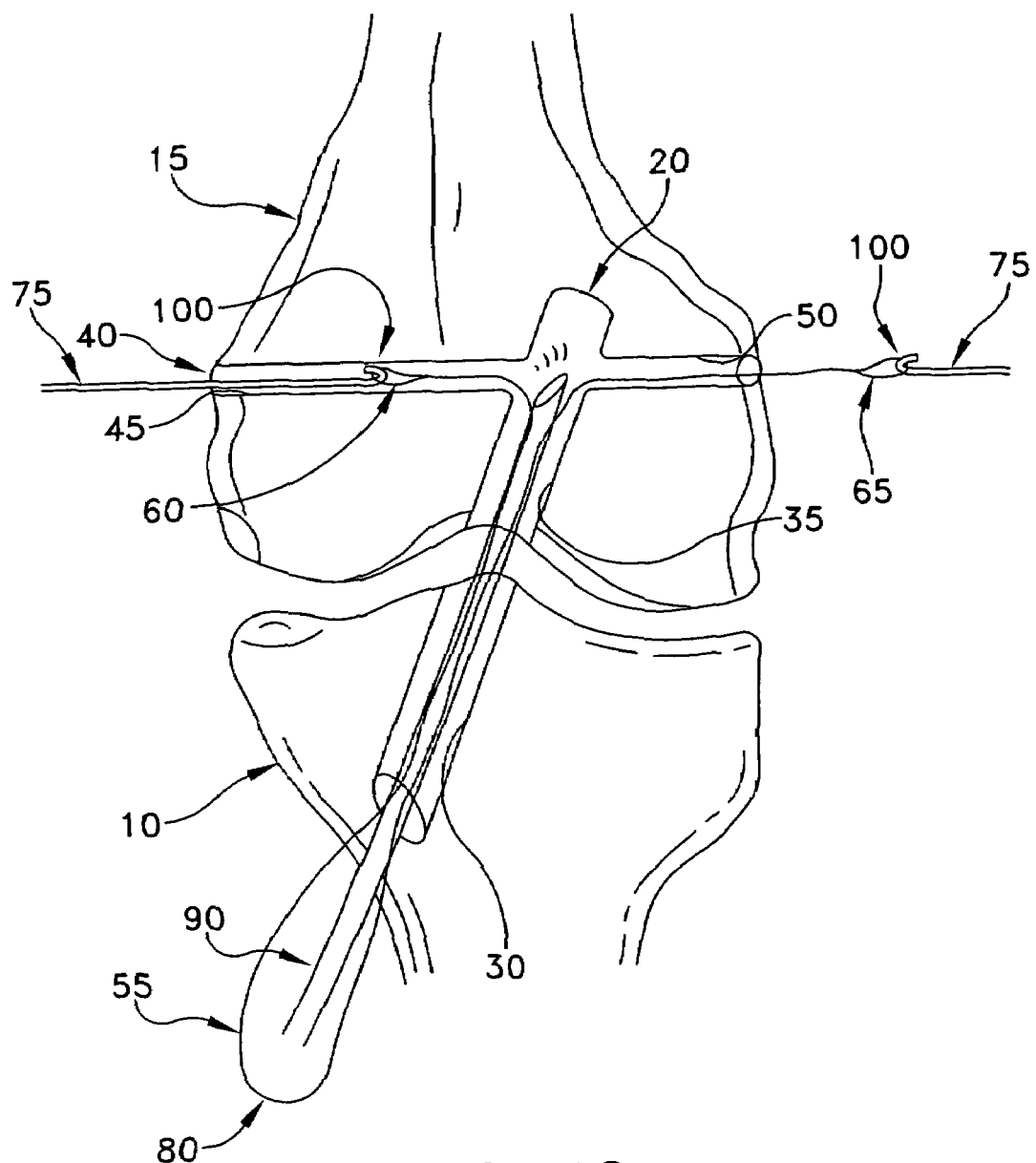

Next, as shown in FIGS. 10-12, first and second ends 60, 65 are drawn through transverse bone tunnel portions 45, 50. Where first and second ends include loops 60A, 65A, this may be accomplished by using a hooked-shaped pulling device 75. Pulling device 75 hooks and draws first and second ends 60, 65 through transverse bone tunnel portions 45, 50, respectively. See FIGS. 10-12. Alternatively, where first and second ends 60, 65 do not include hooks 60A, 65A, pulling device 75 may include needle-nose pliers or the like at its distal end to pick up and extract first and second ends 60, 65.

Delivery device 70 is then withdrawn from bone tunnel 20. At this point, the middle portion of flexible member 55 extends out of tibial tunnel 30, as shown generally at 80. See FIGS. 10-13.

Next, and looking now at FIG. 13, graft ligament 25 is looped through flexible member 55 at the middle portion of flexible member 55, as shown generally at 80.

First and second ends 60, 65 of flexible member 55 are then pulled away from femur 15, in the manner shown in FIG. 13, whereby to pull flexible member 55, and hence graft ligament 25, up tibial tunnel 30, across the interior of the knee joint, and up femoral tunnel 35 so as to achieve the position shown in FIG. 14.

In this respect it should be appreciated that, with the present invention, flexible member 55 is drawn through bone tunnel 20 only once, i.e., at the time that graft ligament 25 is hoisted into position in femoral tunnel 35. This is in contrast to the method taught in the aforementioned U.S. Pat. No. 5,918,604, where flexible member 55 is drawn through bone tunnel 20 twice, i.e., once when flexible member 55 is drawn down bone tunnel 20 to pick up graft ligament 25, and then a second time when graft ligament 25 is drawn back up through bone tunnel 20. Accordingly, the method of the present invention will cause less bone erosion than the method disclosed in the aforementioned U.S. Pat. No. 5,918,604.

Figure 15:
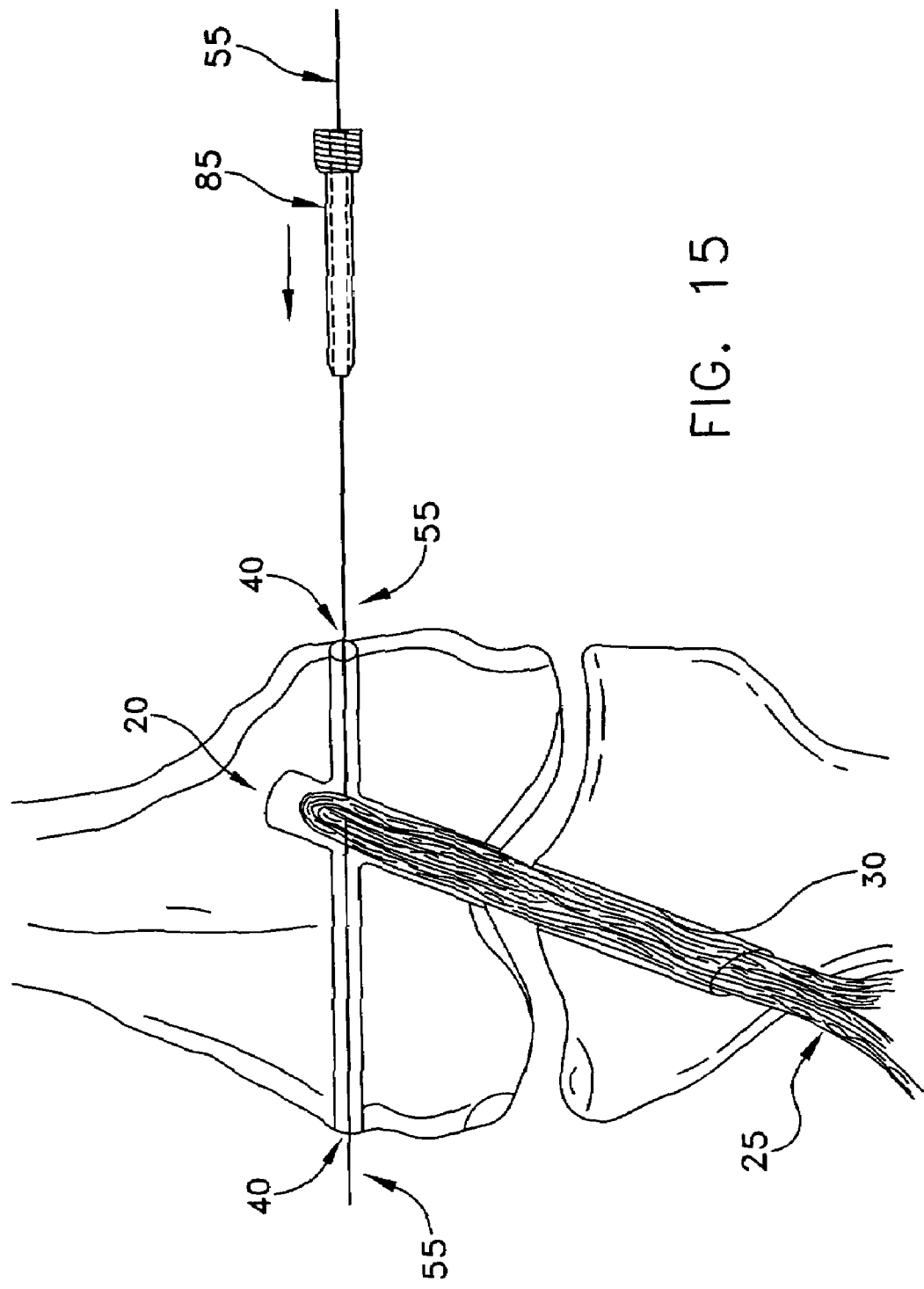

Looking next at FIG. 15, flexible member 55 is then used as a guide to pass a crosspin 85 through transverse bone tunnel 40 and, in the process, beneath looped graft ligament 25, whereby to support graft ligament 25 within bone tunnel 20. Flexible member 55 may then be removed from transverse bone tunnel 40. The proximal end of the graft Ray thereafter be secured to tibia 10 in ways well known in the art so as to complete the ligament repair procedure.

Looking again at FIGS. 6-9, the preferred embodiment of delivery device 70 is cannulated such that an arthroscope 90 may be received therein. This configuration aids in visualizing placement of the ends 60, 65 of flexible member 55 in femoral tunnel 35 and in the pick-up and extraction of those ends through transverse bone tunnel portions 45 and 50. For clarity of illustration, the schematic diagrams of FIGS. 6 and 10-12 show only the first and second ends 60, 65 of flexible member 55, and arthroscope 90, and omit delivery device 70 from the views.

Figure 7:
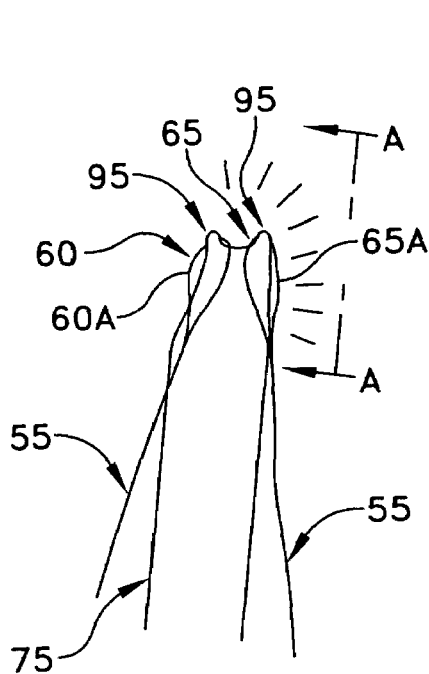
FIGS. 7-9 are schematic views of a flexible member delivery device comprising a cannulated body containing an arthroscope.
Figure 8:
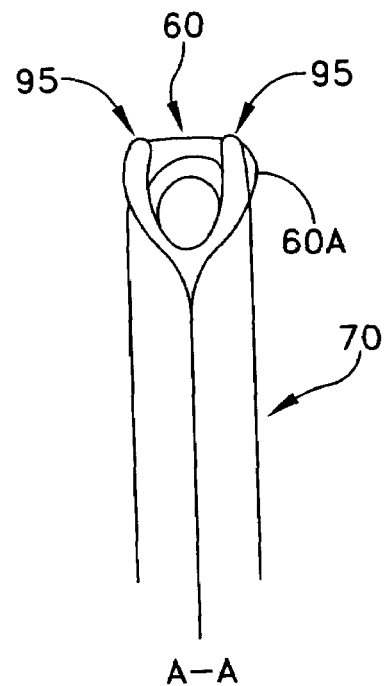
Figure 9:
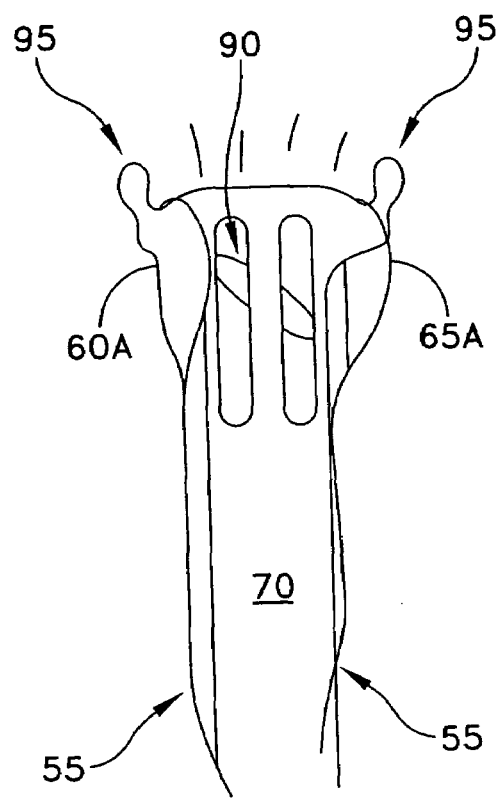

In the preferred embodiment, the ends 60, 65 of flexible member 55 are looped as shown at 60A, 65A. In such a configuration, hooks 95 on delivery device 70, and hook 100 on pulling device 75, secure flexible member 55. Hooks 95 on delivery device 70 carry looped ends 60A, 65A through bone tunnel 20. Looped ends 60A, 65A are then removed from delivery device 70 by hook 100 on pulling device 75, and flexible member 55 is pulled through bone tunnel 40. Inasmuch as hooks 95 and 100 are not actuating elements, the amount of hardware, and the manipulation of this hardware, is minimized. FIGS. 7 and 8 show hooks 95 inboard of the outer perimeter of the shaft of delivery device 70. FIG. 9 shows an alternative embodiment with two hooks 95 outboard of the outer perimeter of the shaft of delivery device 70.

In other embodiments, ends 60, 65 of flexible member 55 may be without loops. In such a configuration, delivery device 70, and pulling device 75, may grasp ends 60, 65 with suture grasping devices (not shown) in ways well known in the art, e.g., with opposing jaws. As such, one or more grasping device(s) on delivery device 70 retain ends 60, 65 of flexible member 55 until pulling device 75 takes hold of ends 60, 65. Pulling device 75 then draws each end 60, 65 through first and second transverse bone tunnels 45, 50, respectively.

ADVANTAGES OF THE INVENTION

Numerous advantages are achieved by using the present invention.

For one thing, manipulation of flexible member 55 vis-a-vis bone tunnel 20 and transverse bone tunnel 40 is easier to effect than with other methods.

In addition, flexible member 55 is less likely to twist when first and second ends 60, 65 are passed up bone tunnel 20 and then out transverse bone tunnel 40.

And, since flexible member 55 is not drawn down bone tunnel 20, the erosion caused by flexible member 55 engaging the bone located at the intersection of femoral tunnel 35 and transverse tunnel 40 is decreased.

Still other advantages of the present invention will be apparent to those skilled in the art.

MODIFICATIONS

It is to be understood that the present invention is by no means limited to the particular construction and method steps disclosed above and/or shown in the drawings, but also comprises any modifications or equivalents within the scope of the claims.

What is claimed is:

1. A system for securing a graft ligament in a first bone tunnel, the system comprising:
   a flexible member for positioning the graft ligament in the first bone tunnel, said flexible member having a first closed loop at a first end thereof; and a second closed loop at a second end thereof, said flexible member being configurable into a generally U-shape with the first and second closed loops being thereby positionable adjacent each other and aligned with each other in the first bone tunnel;
   a delivery device having an end for releasably and simultaneously supporting the first and second loops of said flexible member in adjacency and in alignment with each other, and positioning the first and second loops in the first bone tunnel and in a second bone tunnel extending transversely to and intersecting the first bone tunnel; and
   a pulling member having an end insertable into the second bone tunnel for engaging and withdrawing a selected one of the ends of said flexible member from said delivery device when said delivery device is positioned in the first and second bone tunnels and for pulling the selected end of said flexible member through a portion of the second bone tunnel.

2. A system according to claim 1 wherein the end of delivery device comprises hook means for releasably supporting both of the first and second loops.

3. A system according to claim 1 wherein the end of delivery device comprises first and second hooks for supporting the first and second loops respectively.

4. A system according to claim 1 wherein delivery device comprises a suture supporting device at the end thereof.

5. A system according to claim 1 further comprising an arthroscope associated with said delivery device to aid in visualization of positioning and grasping the first and second ends of flexible member.

6. A system according to claim 5 wherein said delivery device is cannulated and said arthroscope is disposed within cannulated delivery device.

7. A system according to claim 1 wherein the end of said pulling member comprises a hook.

8. A system according to claim 1 wherein the end of said pulling member comprises a suture grasping device.

9. A system according to claim 1 wherein said pulling member is adapted to withdraw either end of said flexible member from delivery device.

10. A system according to claim 1 further comprising a second pulling member, and said first-mentioned pulling member and said second pulling member are adapted to first withdraw the first and second loops from said delivery device and then extract the first and second ends of said flexible member from opposite ends of the second bone tunnel.

11. A system for securing a graft ligament in a first bone tunnel, the system comprising:
   a flexible member for positioning the graft ligament in the first bone tunnel, said flexible member having a first closed loop at a first end thereof and a second closed loop at a second end thereof;
   a delivery device for inserting the first and second loops in the first bone tunnel, said delivery device having means at one end for releaseably and simultaneously supporting the first and second loops adjacent to one another and in alignment with each other;
   a pulling member having an end insertable into the second bone tunnel for engaging and for withdrawing a selected one of the loops from said delivery device when said delivery device is positioned in the first bone tunnel and for pulling the selected end of flexible member through a portion of a second bone tunnel which intersects, and extends transversely to, the first bone tunnel.

* * * * *